United States Patent [19]

Kuwik et al.

[11] 4,266,135

[45] * May 5, 1981

[54] METHOD OF DETERMINING COLLIMATOR APERTURE EFFICIENCY AND APPARATUS WITH AN EFFICIENT COLLIMATOR APERTURE SIZE

[75] Inventors: John J. Kuwik, Hudson; Arthur B. Braden, Solon; Samuel K. Taylor, Chardon; John Covic, Wickliffe, all of Ohio

[73] Assignee: Ohio Nuclear, Inc., Solon, Ohio

[ * ] Notice: The portion of the term of this patent subsequent to Feb. 26, 1997, has been disclaimed.

[21] Appl. No.: 973,570

[22] Filed: Dec. 27, 1978

Related U.S. Application Data

[63] Continuation-in-part of Ser. No. 812,317, Jul. 1, 1977, Pat. No. 4,190,773.

[51] Int. Cl.³ .......................... A61B 600; G01N 23/08
[52] U.S. Cl. ................................. 250/445 T; 250/505
[58] Field of Search ................... 250/445 T, 360, 505, 250/509, 514

[56] References Cited

U.S. PATENT DOCUMENTS

| 4,097,747 | 6/1978 | Kowalski | 250/514 |
| 4,101,768 | 7/1978 | Lill | 250/509 |
| 4,145,610 | 3/1979 | Perilhou | 250/445 T |
| 4,170,853 | 10/1979 | Kohaut | 52/99 |
| 4,190,773 | 2/1980 | Braden et al. | 250/445 T |

Primary Examiner—Alfred E. Smith
Assistant Examiner—T. N. Grigsby
Attorney, Agent, or Firm—Fay & Sharpe

[57] ABSTRACT

The method of determining collimator aperture efficiency for a computerized tomographic scanner having a plurality of radiation detectors positioned along a detector arc, a source of radiation having a focal spot having radiation flux distribution positioned across a scan circle from at least part of the detector arc, and a collimator having a plurality of apertures arranged in a collimator arc around said source.

Also disclosed is a tomographic scanner having a circular detector arc, a radiation source moveable along a circular arc and an arcuate collimator having apertures in which the width of the collimator aperture in the geometry of the system has high efficiency. The ratio of the detector radius to the source radius, to the collimator radius, to the aperture width is 36:24.3;9.4:0.024.

25 Claims, 14 Drawing Figures

METHOD OF DETERMINING COLLIMATOR APERTURE EFFICIENCY AND APPARATUS WITH AN EFFICIENT COLLIMATOR APERTURE SIZE

This application is a continuation-in-part of application Ser. No. 812,317, filed July 1, 1977 entitled "Shutter for Rotary Sources CT Scanners", now U.S. Pat No. 4,190,773.

BACKGROUND OF THE INVENTION

The invention relates generally to the field of radiation imaging of internal structures and, more specifically, to computerized transaxial tomographic (CT) X-ray scanners. Unlike conventional exposed film X-ray apparatus, the CT scanner produces narrow beams of radiation, either X-ray or gamma rays, through plural coplanar paths defining a cross-sectional or tomographic view of the patient's internal organs, such as the brain. The attenuated beams are sensed by radiation detectors whose electrical output is indicative of the intensity of the radiation received by the detector. One of the early types of CT scanners referred to in the patent literature is shown, for example, in Hounsfield U.S. Pat. No. 3,778,614. This system is generally referred to in the art as the "translate and rotate" system. A source and a single detector, for example, are aligned opposite each other on a mechanism which causes the beam path between the source and detector to move laterally across the scan circle. After rotating the source/detector carriage assembly to a new orientation, the translational scan is repeated. Readings are taken at uniformly spaced parallel beam locations and representative values are digitally stored. Data from a full set of scans involving numerous relocations of the beam path is manipulated according to known mathematics involving "back projection" to arrive at a digital representation of the tomographic image. This digital representation is converted to a tomogram which can be viewed on a cathode ray tube. Ohio-Nuclear, Inc. markets a type of translate and rotate CT scanner under the trademark "DELTA SCAN".

The major disadvantage of the translate and rotate system is slowness of the scan mechanism due to the different alternating types of motion. The major advantages of the translate and rotate system are due to the fact that a single detector scans across the entire scan circle thus enabling sampling at any time and avoiding the need to have matched detectors or gain matching.

Another type of scan technique called "purely rotational" employs a fan beam source with a subtended detector array in a fixed relationship such that the fan beam and detector array rotate with each other. This system has a major disadvantage. Numerous detectors are required and none scans across the entire patient. Thus, the sampling resolution is lowered and gain matching of the detectors is required. The major advantage of the purely rotational system is its high scanning speed. The high speed of the scanning motion is desirable to avoid the effect on the image of the resultant displacement of organs due to a patient's breathing.

It has been found that computer image reconstruction can be accomplished with yet another arrangement of source and detectors. In this new system, the detector array is a stationary arc of uniformly spaced detectors about the center point in the scan circle. The fan pattern source revolves about the center point inside the detector array irradiating the scan circle and subtending at any given time only a fraction of the detectors in the total array. If desired, the array may be a complete circle or ring. The reconstruction algorithms are described in Lakshminarayanan, "Reconstruction from Divergent Ray Data", Technical Report No. 92, State University of New York at Buffalo, Computer Sciences Department, January, 1975 and copendent application Ser. No. 838,089, filed Sept. 30, 1977 now U.S. Pat. No. 4,170,835

The new type of scanning system, although requiring numerous detectors and somewhat more elaborate digital processing for reconstructing an image, provides the advantage of high scanning speed due to the single mechanical motion for rotation while also providing the capability of achieving high sampling resolution and avoiding gain matching requirements because each detector views the source across the entire scan circle.

If the circular array of detectors does not fully encircle the patient, it is possible for the patient to be exposed to unused radiation when the source approaches the terminus of its orbit and part of the fan pattern falls outside the detector array. Another problem is presented when the detectors are spaced apart throughout the array since the fan pattern is not aligned with specific detectors but instead floods the scan circle. In this case, a portion of the radiation falls between adjacent detectors and is not used for data collection. This radiation dosage is received by the patient, however, even though it is not used.

An excessive radiation dose problem is presented even when a collimator is used to divide the fan pattern of radiation into finger beams. Because a rotating anode X-ray tube is not a true point or line source of radiation, even a narrow collimator slit will not focus all the radiation on a detector. Rather some of the radiation dosage received by the patient fails to fall within active detector limits.

SUMMARY OF THE INVENTION

The purpose of the invention is to reduce the dosage of unused radiation which the patient receives when a rotating source is used with a series of stationary detectors in a CT scanner system. This is accomplished by employing an eclipsing shutter mechanism to limit the portion of the fan pattern of radiation passing through the scan circle at all times to a width coincident with the subtended portion of the detector array. When the detectors are sufficiently spaced apart in the detector array, unnecessary dosage is reduced by dividing the fan pattern into a plurality of discrete diverging beams and keeping them trained on respective detectors for as long as they are within the scan circle. Unnecessary dosage is further reduced by optimizing the collimator aperture width.

The CT scanner arrangement to which the invention applies is one in which the source rotates and a series of detectors is spaced about the center of rotation coplanar with the orbit of the source. A radiation shield restricts the radiation from the source to a solid fan pattern centered on the axis of rotation. An eclipsing shutter mechanism about the source restricts the fan pattern at all times to a pattern which will fall on the detector array as the source traverses its orbital path. The shutter mechanism may include a single aperture for flooding the scan circle or a multi-apertured collimator, with one aperture for each detector, for training each one of the discrete beams collectively defining the fan pattern on a specific detector for as long as each beam intersects the scan circle. The shutter mechanism is responsive to rotation of the source which causes a specific fractional amount of rotation in the opposite direction as the source moves. When the collimator is employed the respective apertures keep themselves aligned between the source and their respective detectors through the scan circle. In the preferred embodiment, the means for rotating the shutter mechanism is an epicyclic gear train, although other means are possible such as a d.c. motor servo drive, or the like.

Another aspect of the invention is a method of determining the aperture or slit efficiency for collimator slit widths. The slit efficiency or ratio of radiation flux within active detector limits to the total radiation flux passing through a collimator aperture may be used to minimize the unused radiation dosage distributed outside the detector limits.

DESCRIPTION OF THE PREFERRED EMBODIMENTS

Figure 1:
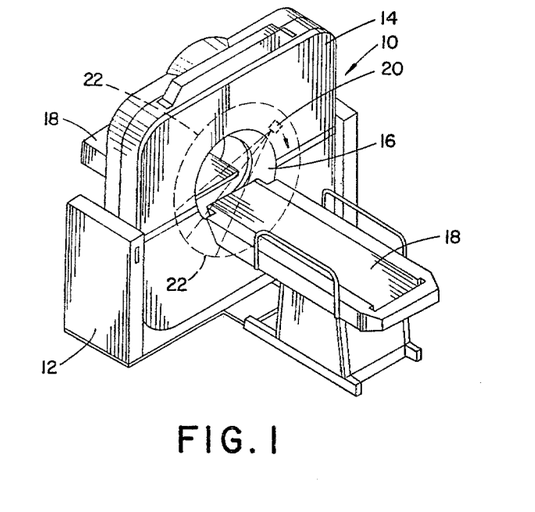
FIG. 1 is a perspective view of CT scanner apparatus associated with the invention.

FIG. 1 illustrates the mechanical apparatus associated with the rotation source type CT scanner system. A gantry assembly 10 includes a U-shaped frame 12 pivotally supporting a gantry 14 having a central circular opening 16 through which a patient is inserted for a body scan, for example, on a two-piece patient table 18. Shown in phantom, the source 20 produces radiation in a coplanar fan pattern directed towards the opposite side of the opening 16 and intersecting the center of the opening 16. Mechanisms within the gantry 14 rotate the source 20 clockwise about an axis through the center of the opening 16 perpendicular to the fan pattern. A ring of detectors 22, also shown in phantom in FIG. 1 is disposed within the gantry 14 concentrically to the opening 16 and at a somewhat greater radius from the center of the opening 16 than the source 20. The detector ring 22 lies in the same plane as the fan pattern. The signals produced by detectors which are within the fan pattern are applied to a number of respective signal processing channels. By using the multiplexing system described in the copending application Ser. No. 783,732, entitled "Data Multiplexing System for CT Scanner with a Rotating Source", filed Apr. 1, 1977 and assigned to the assignee of the present application, the number of signal processing channels can be reduced to the maximum number of detectors subtended by the fan pattern and the detectors can time share these signal processing channels. The copending application is incorporated by reference herein.

Figure 2:
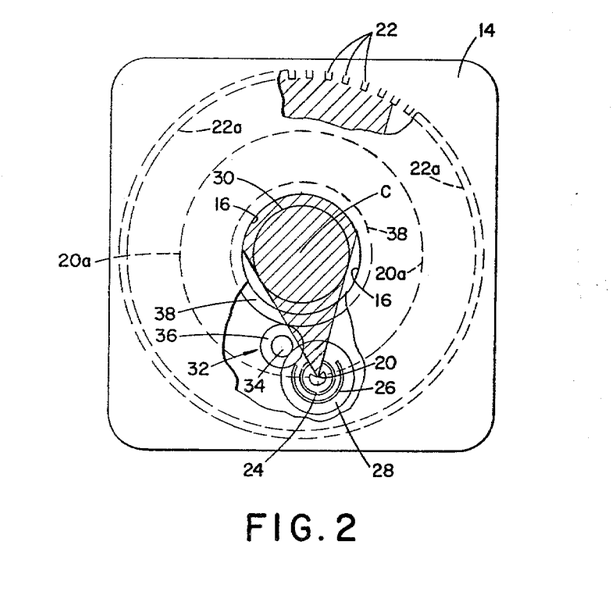
FIG. 2 is a plan view of the gantry with portions broken away to expose the epicyclic gear train driving the shutter mechanism.

In FIG. 2, the view of the gantry 14 shows the source 20 at a low point on its orbit through circular path 20a. The source 20 lines within a radiation shield 24 having a sector missing which causes the radiation directed toward the opening 16 to assume a fan shape. The thickness of the fan in the direction orthogonal to the paper is slightly divergent and at the center of rotation represents the thickness of the slice or tomogram to be reconstructed. Between the source 20 and the opening 16 a shutter mechanism 26 having either a single aperture or a series of very closely spaced apertures concentric to the source 20 is mounted for rotation on a planetary gear 28 rotatable upon an axis coinciding with the source 20.

The source 20 with shield 24 produces a fan pattern of radiation whose angular width determines the diameter of a patient scan circle 30 at a given distance from the center of the scan circle. The scan circle 30 includes the area common to the fan at different positions of the source 20 along its orbit 20a. The area within the scan circle is the area which the reconstructed image will represent. Thus, this area will coincide with the examined portion of the patient's body, for example, the head.

The angular size of the single aperture 26a (FIGS. 4–6) in the shutter mechanism 26 is dependent upon the number and spacing of detectors 22. However, the arc spanned by the aperture 26a in the shutter mechanism is less than the arc spanned by the array of detectors 22. For example, if there are 424 detectors with half-degree spacing from the center line of one detector to the center line of the next detector, they cover an arc of 211° on the detector ring 22a. In the embodiment illustrated in FIGS. 2–6, the resulting arc spanned by aperture 26a in the shutter mechanism is only 127.2°, i.e., 60% of the arc spanned by the detector array.

Figure 3:
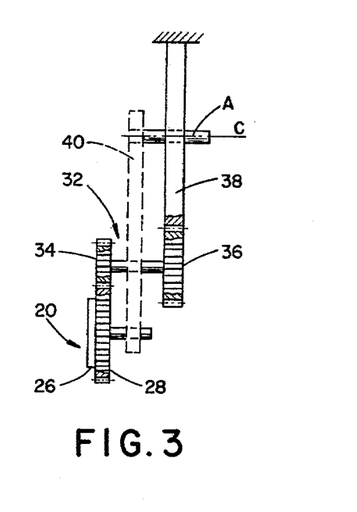
FIG. 3 is a side schematic detail view of the epicyclic gear train.

With reference to FIGS. 2 and 3, a compound gear 32 is used to drive the planetary gear 28 on which the source 20, fan shield 24 and shutter 26 are arranged. Compound gear 32 includes a smaller spur gear 34 driving the planetary gear 28 and a larger spur gear 36, connected for rotation with smaller gear 34, engaging a stationary ring-shaped sun gear 38 affixed to the gantry and concentric with the scan circle about center c. As the source 20 orbits in a clockwise direction along its path 20a, the compound drive gear 32 is caused to rotate clockwise which in turn causes the planetary gear 28 and shutter 26 to rotate counterclockwise. As shown in FIG. 3 in schematic form the axes of the gears are all fixed with respect to each other. For purposes of illustration, this is indicated by arm 40 of FIG. 3 to which the imaginary axle A of the sun gear 38 coinciding with the center c of the scan circle is journalled along with the common axle of the compound gear 32 and the axle of the planetary gear 28. Since the sun gear is fixed, the arm 40 is free to rotate about the imaginary axle A. This rotation produces the orbit of the source 20 with shield 24. This motion is analogous to a solar, planet and moon system in which the sun gear 38 represents the sun, the source 20 represents the earth and a fixed point on the planetary gear 28, for instance, the aperture in the shutter mechanism 26 represents the moon.

Figure 4:
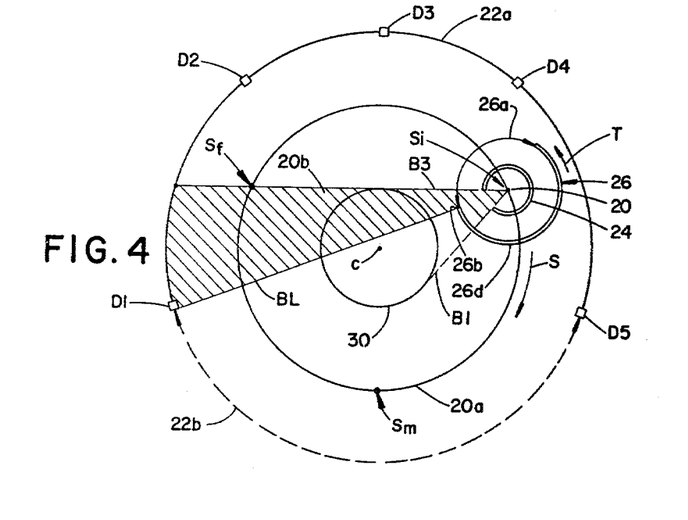
FIGS. 4, 5 and 6 are schematic representations of the relative positions of the source, shutter mechanism, resulting fan pattern and detectors at three different orientations.
Figure 5:
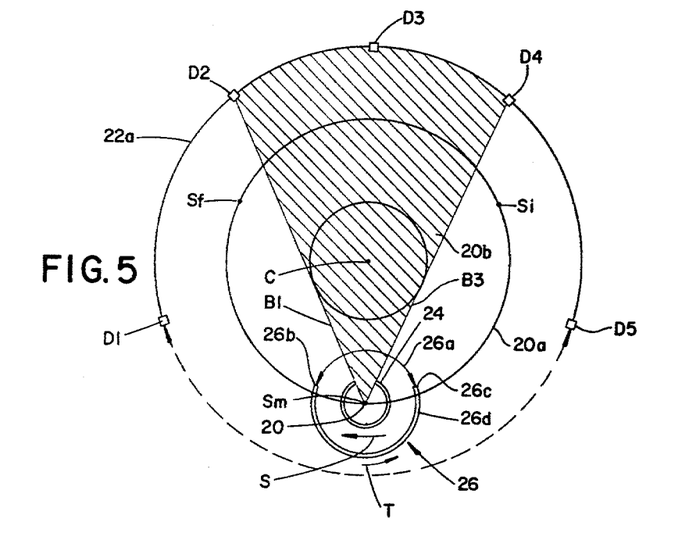
Figure 6:
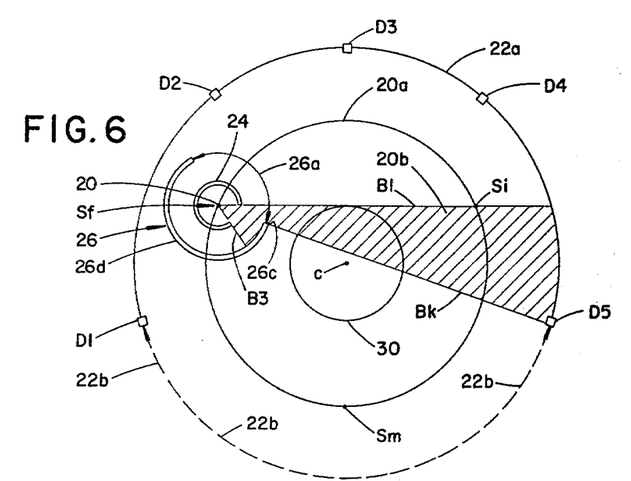

The requirement for this type of motion between the shutter mechanism and the source is demonstrated in FIGS. 4, 5 and 6 showing progressive clockwise orientations of the source. In FIG. 4, the source is shown at the initial point $S_i$ of the scan cycle. In FIGS. 5 and 6, the source is shown at the midpoint $S_m$ of the scan cycle and at the final or end-point $S_f$ of the scan cycle, respectively. FIGS. 4, 5 and 6 also show detector ring 22 and, for illustration, the first, last and three intermediate stationary detectors D1, D2, D3, D4 and D5 in the ring. Of course, in the practical embodiment there are many detectors in the spaces between detectors D1-D5. The arc 22a is bounded by detectors D1 and D5 and defines the detector array span. Arc 22b is that portion of the detector ring which is outside the detector array.

In FIG. 5, the source 20, with shield 24, produces an X-ray field defined by the fan pattern 20b having outer, diverging boundaries B1 and B3 which define the included angle of the fan pattern which floods the scan circle 30. As shown in FIGS. 4 and 6, the eclipsing shutter mechanism 26 acts to reduce the included angle of fan pattern 20b whenever the source approaches either terminus $S_i$ or $S_f$ of its cycle. This is desirable because the array of detectors on ring 22 does not entirely encircle the scan circle and if the width of the radiation field was not so restricted, unused radiation would pass through scan circle 30 and needlessly increase the patient dosage.

The eclipsing effect of the shutter 26 is accomplished by utilizing the epicyclic mechanism of FIG. 3. It should, of course, be understood that other drive mechanisms such as, by way of example, a d.c. motor servo drive may also be employed. In the illustrated embodiment, the included angle between the first detector D1 and the last detector D5 is 212°. The remaining arc 22b of ring 22, 148° in the example, is outside the detector array. The shutter mechanism 26 is utilized to preclude the projection of any portion of the X-ray of fan pattern 20b through the scan circle if that portion of the field would fall outside the detector array, i.e., on arc 22b.

With the arrangement shown in the drawings, a 60% rotation of shutter 26 is required for each 100% positive rotation of source 20 about its orbital path 20a. The source moves from point $S_i$ to point $S_f$ on path 20a in the direction of arrow S during a scan cycle, and the shutter rotates in the opposite or negative direction as indicated by arrow T. As shown in FIG. 4, the leading edge 26b of the shutter aperture is on a straight line projecting from detector D1 to source 20 for as long as a straight line projecting from detector D1 to the source intersects the scan circle 30. Thus, the shutter imposed boundary $B_L$ of fan pattern 20b is trained on detector D1 continuously for as long as the detector is in the data-taking portion of the scan cycle. There may be some minor deviation of the imposed boundary $B_L$, which is in effect the same as the deviation of an individual slit in the rotating collimator described below. The portion of the fan pattern between the trailing edge B1 of the fan pattern and the shutter imposed boundary $B_L$ is blocked by the shielding portion 26d of shutter 26 and does not pass through the scan circle 30. This is desirable since this portion of the fan pattern would fall outside the detector array and would needlessly increase the patient's exposure to radiation.

As the source traverses about its orbital path 20a in the direction of arrow S (clockwise), the shutter 26 rotates in the direction indicated by arrow T (counterclockwise) 0.6° for every 1° of source rotation, ever increasing the fan pattern width while continuously training the shutter imposed boundary $B_L$ of the fan beam on the detector D1 for as long as the detector D1 is in the data-taking portion of the cycle, i.e., the scan circle is intermediate the detector D1 and the source 20. The fan pattern continues to widen until the entire fan pattern bounded by leading edge B3 and trailing edge B1 falls on the detector array. At this point, the shutter aperture is completely out of the path of the fan pattern emanating from source 20 and the entire fan pattern floods the patient scan circle 30. This is desirable since the entire fan pattern falls on the detector array.

The source 20 is shown at the mid-point $S_m$ of its travel in FIG. 5. This is representative of the flooded scan circle wherein the leading edge B3 of the fan pattern 20B falls on detector D2 and the trailing edge B1 falls on detector D4. As the source 20 continues its movement, leading edge B3 of the fan pattern approaches detector D5, the last detector in the array. Again, it is desirable to block any portion of the fan pattern which will fall outside the detector array span. At this point, illustrated in FIG. 6, trailing edge 26c of the shutter aperture has rotated into blocking relationship with the source and shields the leading edge B3 and a portion of the fan pattern 20b, training the shutter imposed boundary $B_K$ on the last detector D5 for as long as the detector D5 is in the data-taking portion of the scan cycle. After the source has completed its orbital cycle by traversing to point $S_f$, both the source and the shutter are returned to the initial position $S_i$ of FIG. 4.

By utilizing the shutter mechanism 26, the source can be rotated through any portion of its orbital path without passing any radiation through the scan circle that does not ultimately fall on the detector array span. The single apertured shutter mechanism 26 of FIGS. 1-6 is practical whenever the detectors in the detector array are spaced in such a manner that it is desirable to flood the scan circle with radiation.

It is possible to further reduce the patient dosage by subdividing the fan pattern into a plurality of discrete beams, each trained on a particular detector for as long as the detector is in the data-taking portion of the scan cycle. In another embodiment of the present invention, this beam subdivision is illustrated for a system in which the center lines of adjacent detectors 22 are spaced apart approximately one half degree about the detector ring.

The beam subdivision is accomplished by replacing the single-apertured shutter 26 with a multi-apertured shutter or collimator 126 as shown in FIGS. 7-10. The first and last apertures in the rotating collimator effectively perform the same function as the trailing and leading edge of the eclipsing shutter. The number of apertures in the collimator 126 corresponds to the number of detectors 22. However, as with the single-apertured shutter 26, the arc spanned by the apertures in the collimator 126 is less than the arc spanned by the detectors 22. For example, if there are 424 detectors with 1/2° spacing from the center line of one detector to the center line of the next detector, they cover an arc of 212° on detector ring 22a. There would be 424 closely machined apertures in the collimator 126, one for each detector. However, as with the shutter aperture 26a, the arc spanned by the 424 apertures is again only 127.2°, i.e., 60% of the arc spanned by the detector array in the geometry of the embodiment illustrated.

Figure 7:
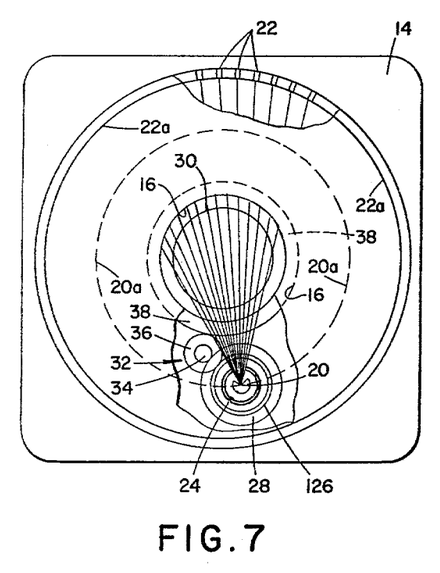
FIG. 7 is a plan view, similar to FIG. 2, showing a shutter mechanism having a multi-apertured collimator and the resulting discrete, diverging beams of the fan pattern.

The apertures in the collimator 126 make a plurality of narrow discrete diverging equally, angularly spaced beams which collectively form the fan pattern 20b whose angular width at a given distance from a scan center determines the diameter of the patient's scan circle 30. The object of the collimator 126 is to keep each beam of fan pattern 20b aimed toward a specific single detector while the source 20 moves along the path 20a. Of course, this is only of importance while the line between the particular detector and the source intersects the scan circle 30. The line will intersect the scan circle over the angle defined as the "detector angle" subtended from the detector by the diameter of the scan circle.

Figure 8:
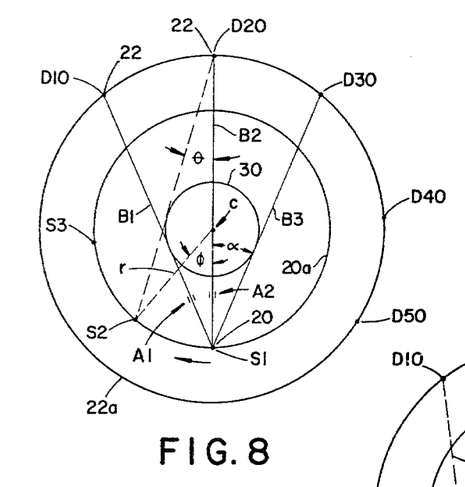
FIGS. 8, 9 and 10 are schematic representations of the relative positions of the source, collimated beams and detectors at three different orientations.
Figure 9:
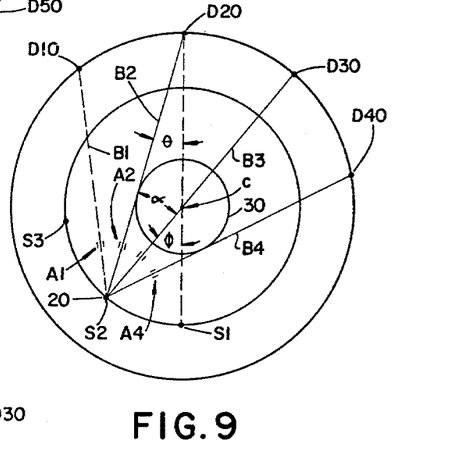
Figure 10:
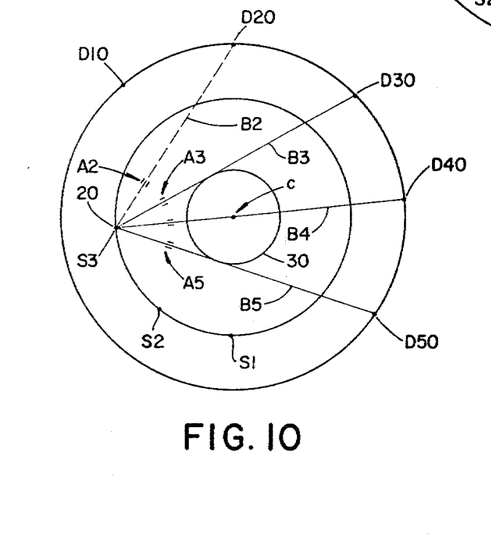

The epicyclic motion between the collimator ring and the source is demonstrated in FIGS. 8, 9 and 10 showing progressive clockwise orientations of the source separated by 40°. FIG. 8 shows three successive source positions S1, S2 and S3 each separated by 40° as the source traverses orbit 20a in the clockwise direction. FIG. 8 also shows detector ring 22 and, for illustration, five stationary detectors D10, D20, D30, D40 and D50. Source 20 produces a fan of plural diverging beams centered collectively on the center c of rotation of the source 20. Three of these plural beams B1, B2 and B3 have been selected for FIG. 8 because of their geometric significance. As in FIGS. 4–6, beams B1 and B3 are the peripheral beams of the fan beam pattern and are tangent to the scan circle 30. Beam B2 passes through the center c. The fan beam width is twice $\alpha$, where $\alpha$ is the angle made by beams B2 and B3. In practice, there are many beams between B1 and B2 and B2 and B3. Likewise, there are many detectors between each one of the five detectors shown in FIG. 8. Detector D10 is defined as the detector lying on the tangent from the source position S1. Detector D20 is aligned with the center and position S1 and detector D30 lines on the other tangent to the scan circle from position S1.

In FIG. 8, beam B2 is defined by aperture A2, one of the apertures in the collimator ring 26 of FIG. 2. In this orientation, the aperture A2 sights the source along the center c. As the source 20 moves from position S1 to S2, it moves through the angle $\phi$ about the center c of rotation. The radius r from the new source position S2 to center c in FIG. 8 indicates the direction in which the aperture A2 would aim the source if aperture A2 were fixed to the source and thus always looking toward the center c. This would mean that beam B2 would no longer be looking at detector D20 but would be looking in the direction of detector D30. While the source is moving from position S1 to S2, it is not desirable for the beam B2 to move its target along the path from D20 to D30. Instead, beam B2 should be continuously trained on detector D20 as shown in FIG. 9. This requirement dictates that aperture A2 will not be aligned with the radius but rotate through the angle $\alpha$ to a new angular orientation about the source 20 such that the beam B2 remains directed at detector D20. While the source is moving from S1 to S2 through angle $\phi$, the aperture A2 must be moving continuously through an angle which grows to angle $\alpha$ at the same time. This means that the aperture A2 has to rotate counterclockwise about the source 20 as the source 20 moves clockwise from position S1 to position S2 in order to keep beam B2 trained on detector D20.

Aperture A2 represents but one of the apertures for the many detectors between detector position D10 and detector position D30 in the practical embodiment. All of the beams have to slued or scanned across the scan circle in the same manner as B2. For example, beam B3 has just come into being, that is, has just intersected the scan circle 30 and for the first time detector D30 is illuminated by radiation from B3. As the source 20 moves from position S1 to S2, beam B3 remains trained on the detector D30 as shown in FIG. 9. The only way that this can be accomplished is for its corresponding aperture A3 to rotate the same amount and sense or direction as aperture A2. Thus, in FIG. 9, beam B3 views detector D30 through the center c although before in FIG. 8, beam B3 started out on the periphery of the scan circle 30. At the time shown in FIG. 8 detector D10 is at the point where it is about to lose communication with the radiation fan altogether. Beam B1 has been slued all the way across the scan circle 30 to its periphery and as the source begins to move clockwise from position S1 even slightly, the beam B1 trained on detector D10 by corresponding rotating aperture A3 falls outside of the scan circle 30 and is darkened by the fan shield 24 shown in FIG. 2. Thus, the beam B1 shown in FIG. 9 after the source has moved to position S2 is only imaginary since it is blocked by the shield 24. The only active beams in FIG. 9 are those beams B2, B3 and new beam B4 which has just become tangent for the first time with the scan circle 30. Aperture A4 trains beam B4 on detector D40.

In FIG. 10, after the source 20 has moved through another 40° clockwise to position S3, beams B1 and B2 are no longer in use and new beam B5 trained on detector D50 through aperture A5 has come into view, tangent to the scan circle 30. By the time shown in FIG. 10, beam B3, which came into view for the first time in position S1 in FIG. 8, has been slued through the center c of the scan circle 30 in FIG. 9 and is now tangent for the last time to the scan circle 30 just before it will pass out of view. The aperture A2 which was originally centered on the center c in FIG. 8 has by the time the source has moved through 80° in FIG. 10 moved around the source S3 so far that it is no longer even sighting the source through the scan circle.

It is important to note that the angle through which aperture A2 has moved is not 80°; it is less than 80° because of the geometry of the source and detector arrangement. The ratio of the angular velocity of the source to the angular velocity of the aperture A2 or any other aperture on the collimator (or the single aperture 26a of FIGS. 1–6) is determined by the relationship between the radius of the source orbit and the radius of the detector ring. It can be shown that there are values for these two radii at which the ratio of the angular velocities of the source about the center c and the collimator ring (or shutter 26 in FIGS. 1–6) about the source 20 are rational numbers which can be accommodated by a reduction gear train. For example, it can be shown that if the detector ring has a radius of 36" and the source has a radius of 24.3", the angular velocity of the collimator (or shutter in FIGS. 1–6) around the source 20 should be exactly 60% (in the opposite direction) of the angular velocity of the source 20 about the center c. This ratio ($-0.60$) is relatively amenable to a toothed gear train solution.

It can also be shown that if the detector ring is kept at 36" and the source is moved from 24.3 to 24.0" that the angular velocity ratio becomes −0.603015. This ratio cannot be practicably resolved with a simple gear train. Although it is true that a friction drive of appropriately sized wheels might accommodate such a ratio, the dimensional instabilities in a friction drive assembly make it appear to be inappropriate for accurate registration of the collimator assembly. Toothed gears on the other hand are extremely accurate because there is no slippage allowed. This same relationship holds true when the single apertured shutter 26 of FIGS. 1–6 is utilized.

There is another anomalous factor at work in the geometry of FIGS. 8–10. Even with the "best" angular velocity ratio, namely 0.603015 for a source location of 24.0", the beams do not tract the detectors perfectly, that is, there is a slight aberration or error as the source orbits. The center line of a given beam, although aimed in the direction of a particular detector, will travel slightly over the center line of the detector.

There is another reason why the location of the source at 24.0" would have been undesirable. A very minor change in the source location from 24.0" to 24.3" not only caused the angular velocity ratio to become a rational number (−0.6000) but also at the same time it reduced the error of the beam tracking to within a range of plus or minus 1.037 to 1.078 millimeters. This tracking linearity error was calculated for the condition where the X-ray beam is emitted through particular aperture over approximately 80° of source rotation, the full angle in FIG. 8 through which each beam is slued through the scan circle 30.

These dimensions are, in fact, used for the preferred embodiment, a commercial model of which is under development by the assignee. Thus, with the source orbit at 24.3" and the center of each detector face at 36.0", the ratio of −0.60 for the angular velocities of the source and collimator or shutter is accomplished by the following gears, referring to FIG. 3: the sun gear 38 has 600 teeth; the larger compound gear 36 engaging the sun gear 38 has 100 teeth; the smaller compound gear 34 engaging the planetary gear 28 has 40 teeth and the planetary gear 28 has 400 teeth. The ratio of the number of teeth on the sun gear 38 to the number of teeth on the larger compound gear 36 multiplied by the ratio of the number of teeth on the smaller compound gear 34 to the number of teeth on the planetary gear 28 is 0.600. Any other kind of epicyclic gear train that reverses the sense of rotation of the planetary gear and collimator ring 26, and provides a reduction of exactly 60% will do. It also appears, because of the circular geometry of the system, that the dimensions of the radii of the source and detector ring will scale properly; that is, the ratio of the detector ring radius to the source radius, 1.48, for the preferred embodiment, will require an angular velocity ratio for the collimator and source of exactly 60% no matter what the size of the system. With a detector spacing of ¼° of collimator, aperture width of 0.60 mm, an outer collimator radius of 9.40 inches is preferred. Other geometries of source diameter, detector diameter and collimator diameter can be used provided the corresponding adjustments to the gear ratios in the gear train are made.

Figure 11:
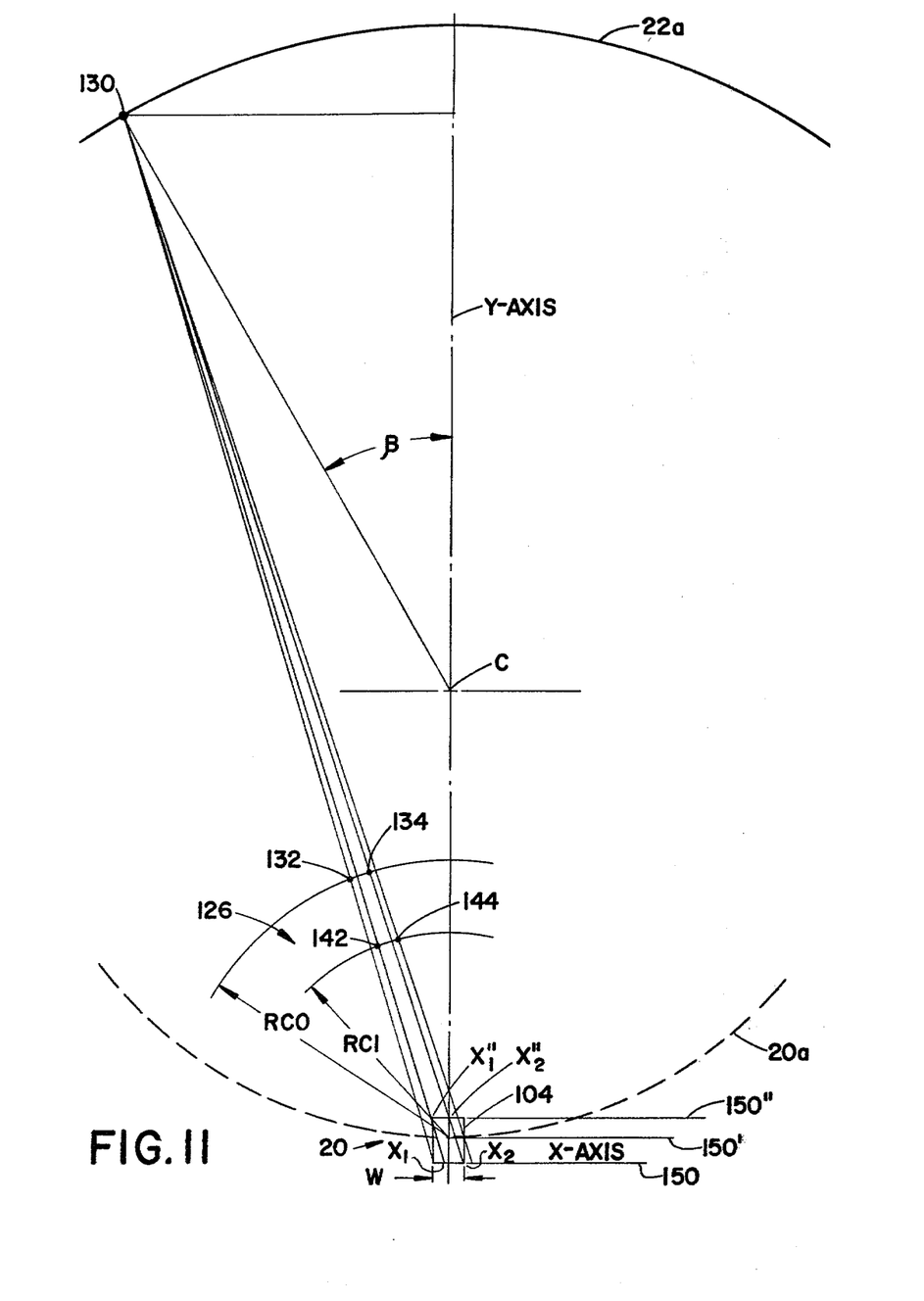
FIG. 11 is a schematic diagram of a CT scanner with collimator showing projection lines.

FIG. 11 shows a schematic diagram of the geometry of a computerized tomographic scanner to which reference is made in explaining the method of determining collimator aperture efficiency. Briefly stated the method entails determining the amount of radiation impinging upon arc 22a and the amount of radiation impinging on that portion of the arc that the detectors occupy. 100% efficiency is achieved when all the radiation impinging on arc 22a impinges on detectors and none in between.

The amount of radiation impinging on any point of the arc 22a is affected by several factors. These include the geometry of the system, especially the degree of alignment between the point, a collimator aperture and the source, the size of the aperture and the size and energy distribution of the source. The size relationships of FIG. 11 have been distorted from the above dimensions for clarity of representation of the principals of the method. Position along arc 22a is described in terms of the angular displacement $\beta$ along arc 22a.

As explained above, for each detector there is a specific aperture in collimator 126 which remains positioned between the source 20 and the detector. Thus, for $\beta$ corresponding to the center of a detector there is an aperture positioned about a line from the center of the detector to the center of the source. For a point not at the center of detector an aperture is at best only partially aligned between the source and the point. For example, radiation impinging upon a point 130 on arc 22a has passed through an aperture in collimator 126 defined by points 132 and 134 on the outer periphery of the collimator a distance RCO from the source and by points 142 and 144 on the inner periphery of the collimator a distance RCI from the source.

From the perspective of a detector, there are four readily demarcatable paths which could mark the extremes of possible paths between a point on a detector and the radiation source—the paths from the detector through each of the four corners of the aperture. These extreme paths are represented by four lines drawn from point 130 through points 132, 134, 142 and 144 which mark the corners of the collimator aperture. Of course, only two of these four paths can mark the actual extremes. Which of the lines through 132 and 142 and of the lines through 134 and 144 mark the boundaries varies with the geometry and the angular displacement $\beta$ of point 130. For any angular displacement $\beta$, one of the lines through 132 and 142 is tangent to the collimator at point 132 or 142, while the other passes at least partially through the collimator structure. A boundary path passing partially through the collimator is physically impossible. Similarly, one of the paths through 134 and 144 is also always impossible. The two lines representing valid extremes intercept the source 20, or more precisely, a focal spot 104 of the X-ray tube which forms the source.

These two lines representing the valid extremes delineate the region of focal spot 104 which contributes to the total energy received at point 130. The intensity of radiation flux, I, received at point 130, may be represented mathematically as:

$$I = \int\int f(x,y) dx dy$$

where f(x,y) is the energy distribution across the focal spot and the limits of integration are defined by the lines representing the valid extremes.

For simplicity of evaluation, the double integral may be approximated as:

$$I = \sum_{y=1}^{N} \int_{x_1}^{x_2} f(x) dx$$

where f(x) is the energy distribution along a line cutting the focal spot in the x direction, where $x_1$ and $x_2$ are the intercepts of the valid extreme paths with the cutting line and where the summation is over a plurality of parallel cutting lines. If an intercept is beyond the boundary of the focal spot, the integration is preformed only to the boundry of the focal spot. Because f(x) is periodic in the preferred embodiment, integration should not be carried out beyond the boundary unless f(x) is set to zero in that ragion. The cutting lines are a plurality of parallel imaginary lines across the focal spot along which lines the energy distribution is known.

Any number of cutting lines through the focal spot may be used. Equivalently, one cutting line may be viewed as being shifted incrementally from one edge of focal spot 104 to the other. The integral is evaluated between the intercepts of the valid extremes on each cutting line. In the preferred embodiment, cutting line 150 assumes 8 positions providing 8 contributions to the energy received at point 130. Further the energy distribution is normalized, i.e.

$$\int_{-w/2}^{w/2} f(x)dx = 1$$

where w is the width of the focal spot along the x axis. Thus, the total amount of energy available from along one cutting line of the focal spot is assigned, for each computation, the arbitrary value of 1 unit of energy.

Figure 12:
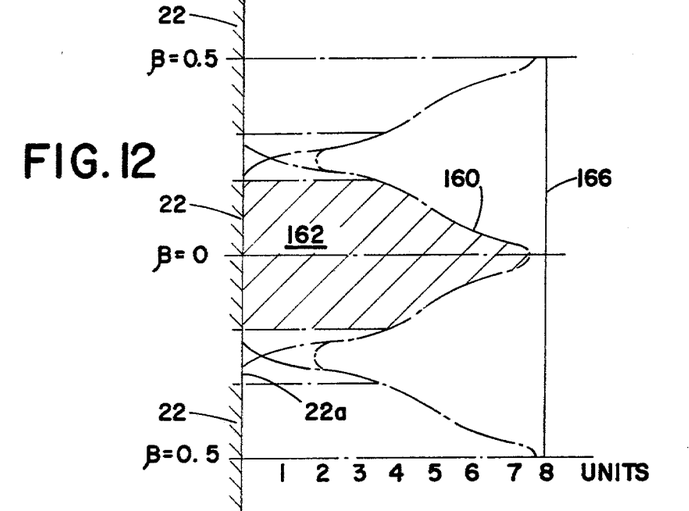
FIG. 12 is a typical radiation intensity distribution along a detector arc segment.

By stepping point 130 incrementally along arc 22a and recaluating the intensity at each point along arc 22a a curve as exemplified by curve 160 of FIG. 12 can be produced. After correlating the radiation detectors 22 with the positions along 22a, the relative amounts of radiation impinging upon and falling between the detectors is determinable.

The efficiency of the collimator is, by definition, that percent of the total radiation flux to which a patient is subjected which impinges upon a detector. This efficiency is determinable from the ratio of the amount of energy impinging upon that portion of arc 22a along which a detector is positioned to the amount of energy impinging upon arc 22a generally. The shaded area 162 represents the energy impinging on the portion of arc 22a which corresponds to a detector. Note that area 162 is both under curve 160 and over a detector 22. The area under one cycle of curve 160 represents the energy impinging on arc 22a generally. In the illustration of FIG. 12, the area 162 is 33.89 units, and the area under one cycle is 39.06. For the amount of energy represented by curve 160, the efficiency is 86.78%. With the open shutter of FIGS. 2, 4, 5, and 6, the amount of energy striking arc 22a is illustrated by curve 166.

The present method can be performed graphically. However, in the preferred embodiment, a computer is programmed to carry out the above analysis. Many programs and languages may be used. The following steps provide one basis for implementation:

1. Assign x, y corrdinates to points 130, 132, 134, 142 and 144.
2. Project lines from point 130 through 132, 134, 142 and 144, hereinafter line 130-132, line 130-134, line 130-142, and line 130-144 to intersect a first cutting line 150 through the focal spot coordinates.
3. Determine the two valid boundary lines, e.g. determine the two lines which have the inner most intercepts.
4. Perform the integration of f(x) between the intercepts of the two valid lines with cutting line 150.
5. Shift the cutting line along the y axis one incremental step to 150'; calculate new intercepts and repeat the integration.
6. Repeat step 5 until the cutting line has been shifted along the y axis a distance equivalent to the length of the focal spot.
7. Sum the products of the integrations.
8. Shift point 130 and repeat the above steps.
9. Calculate the ratio of the total flux impinging on points 130 along the detector arc corresponding to a detector to the total flux passed by the collimator aperture and striking the detector arc.

Alternately, in addition to or instead of step 9 a graphics generating program may generate a print out similar to FIG. 12.

Calculation of the average efficiency over one scan can be achieved by redefining the coordinates of points 130, 132, 134, 142 and 144 and the focal spot to simulate several positions within the radiation fan. The efficiencies at positions spanning the fan or a symeteric half of the fan are plotted or averaged.

By changing the coordinates of points 132, 134, 142 and 144 models of different aperture widths, collimator thickness, collimator sizes, etc. can be created allowing the efficiencies of different collimator systems to be compared.

It will be appreciated that patient dose varies directly with the collimator aperture width, i.e., halving the width halves the dose. However, as seen from curve 160, detector flux does not vary directly with collimator aperature width. In the above scanner geometry, with a detector spacing on the order of $\frac{1}{2}°$, a collimator aperture of 0.60 mm in width reduces the patient dosage to 50% of an uncollimated system; but the above analysis shows that the average detector flux is reduced only to 75% of the uncollimated system.

The energy distribution f(x,y) across the focal spot 104 is not constant. For a rotating anode X-ray tube, microdensitometer examination of the focal spot has shown that the X-rays are emitted primarily along the edges of the focal spot. This has led others to approximate the focal spot as a pair of parallel line sources. Others still have developed such solutions as the dual filament X-ray tube of U.S. Pat. No. 4,065,689 to make a more uniform focal spot distribution.

In the present method, an energy distribution in the form of a pair of parallel line sources has proven to be too inaccurate when applied to very narrow collimator slits. For example, with the above scanner geometry and detectors placed at $\frac{1}{2}°$ of detector arc spacings, a collimator does not appear practical with the parallel line energy distribution.

On the other hand, the actual, physical energy distribution is so complex that evaluation of the above double integral or line integral of the present method is cumbersome.

Figure 13:
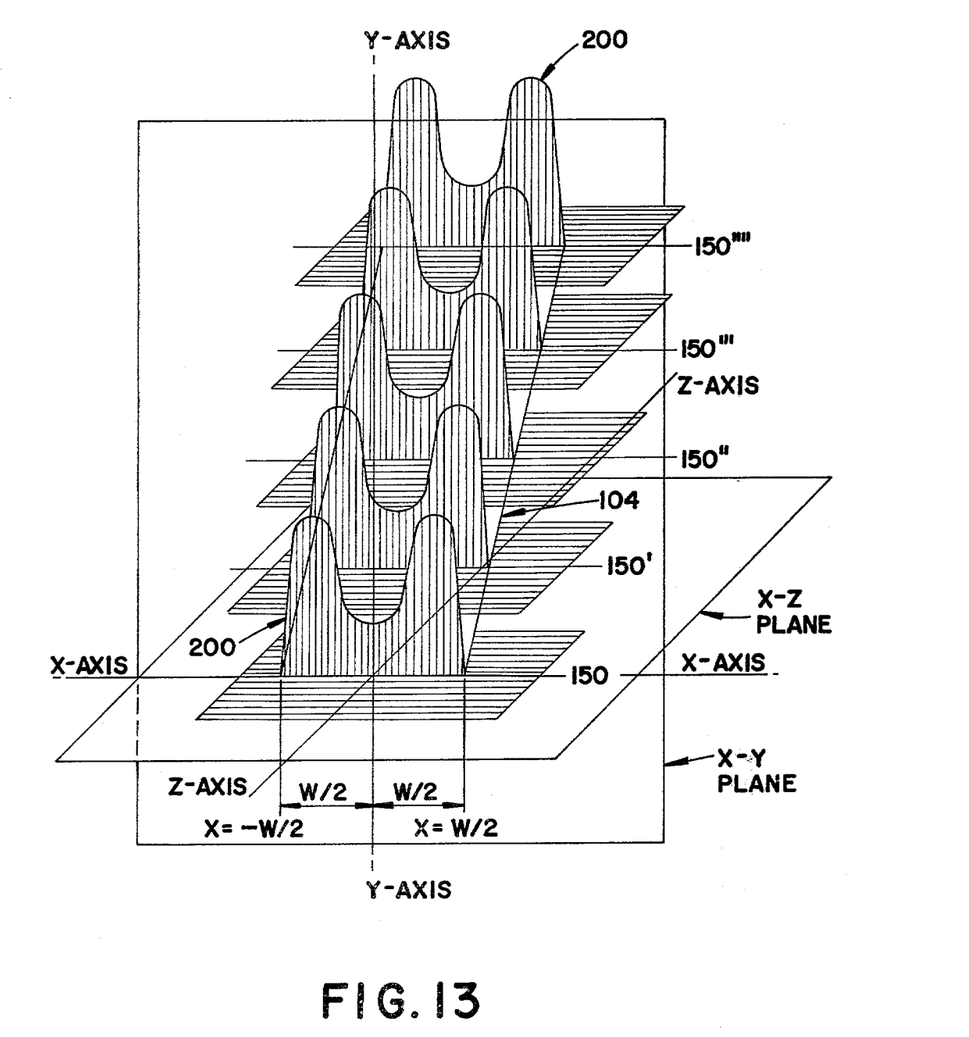
FIG. 13 is an illustration of a preferred model for radiation flux distribution across the focal spot of a rotating anode X-ray tube.
Figure 14:
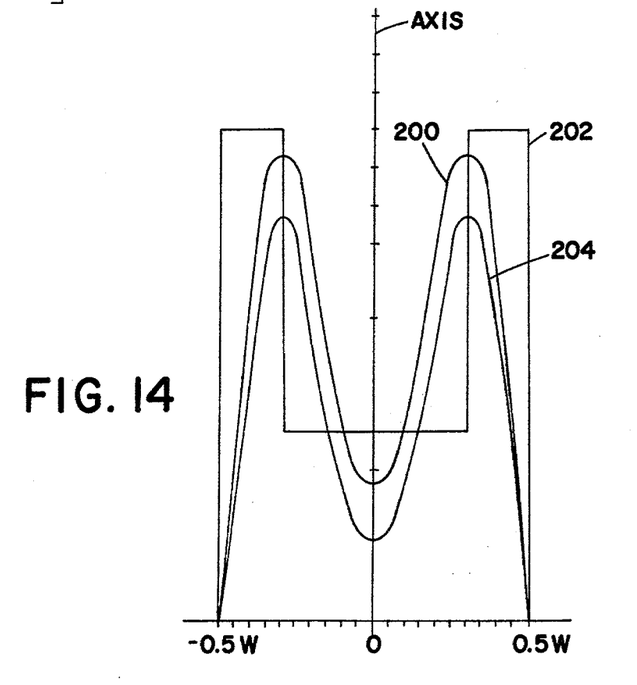
FIG. 14 is a section view of the preferred model of flux distribution of FIG. 13 along the X axis.

To balance sufficient accuracy with ease of interpretation, the energy distribution model of FIG. 13, shown in cross-section in FIG. 14, is preferred. The energy distribution of FIG. 13 has a base corresponding to the focal spot, which is canted 15° from the x, y plane. The amplitude along the y axis represents energy. The distribution is generally in the form of slices through a rounded trough. The cross-section 200 of this distribution is a Fourier series expansion of curve 202 with a d.c. offset added for normalization. To determine the Fourier transform, curve 202 is approximated as a periodic function g(x) defined by:

$$g(x) = \begin{cases} .645/w & 0 \leq x \leq .3w \\ 1.5625/w & .3w \leq x \leq .5w \\ -1.5625/w & .5w \leq x \leq .7w \\ -.625/w & .7w \leq x \leq w \end{cases}$$

where w is the width of the focal spot. The Fourier expansion of g (x) is $$n_{odd} \Sigma a_n \cos \frac{n\pi}{w}$$

where $$a_n = \frac{2}{w} \int_0^w g(x) \cos \frac{n\pi x}{w} dx$$

Selecting the Fourier series with only the first two Euler coefficients, $a_1$ and $a_3$, as the model of the energy distribution f(x) along the cutting line of the focal spot, the mathematical model becomes $$f(x) = \frac{1.023}{w} \cos \frac{\pi x}{w} - \frac{.786}{w} \cos \frac{3\pi x}{w}$$

which is illustrated as curve 204.

To further simplify the method, the total flux, I, from the energy distribution across one cutting line is normalized, i.e., $$\int_{-w/2}^{w/2} f(x)dx = 1$$

Thus, normalized, f(x) becomes:

$$f(x) = \frac{1.023}{w} \cos \frac{\pi x}{w} - \frac{.786}{w} \cos \frac{3\pi x}{w} + \frac{.182}{w}$$

which is shown graphically as curve 200.

Other mathematical models, of course, can be used. For other types of X-ray tubes, it is usually necessary to use other models. However, for rotating anode X-ray tubes, the above model is an exceptionally desirable compromise between accuracy and ease of integration and is, accordingly, preferred.

This invention has been described with reference to the preferred embodiments with some possible modifications thereto. Obviously, other modifications and alterations will be obvious to others upon the reading and understanding of this specification. It is our intention to include all such modifications and alterations insofar as they come within the scope of the appended claims or the equivalents thereof.

We claim:

1. A radiation aperture system for a CT scanner having a rotating source of radiation and a detector array; a series of stationary radiation detectors partially encircling the path of the source in the same plane at less than 1° intervals, the radiation aperture system comprising:
   collimator means for restricting the radiation to an energy distribution having alternating relatively high energy and relatively low energy regions, said collimator means being mounted for rotation about the source; and,
   drive means for causing counter rotation of said collimator means about the source as the source rotates such that each one of said relatively high energy regions is trained continously generally on a single stationary detector during part of rotation of the source.

2. The system of claim 1 wherein the radiation detectors are at generally 0.5° intervals.

3. The system as set forth in claim 2 in which said collimator means includes a plurality of apertures, the number of collimator apertures being substantially equal to the number of stationary detectors.

4. The system as set forth in claim 3 wherein the ratio of the radius of the source path to the width of each collimator aperture is generally 1000:1.

5. The system as set forth in claim 3 wherein the ratio of the radius of the source path to the width of each collimator aperture is 24.3:0.024.

6. The system as set forth in claim 3 wherein the ratio of the radius of the detector array to the width of each collimator aperture is substantially 36:0.024.

7. The system as set forth in claim 3 wherein said collimator apertures are arranged along a generally circular arc and the ratio of the radius of the detector array to the radius of the source path to the radius of the collimator aperture arrangement to the width of each collimator aperture is substantially 36:24.3:9.4:0.024.

8. The system as set forth in claim 3 wherein the width of each collimator aperture is substantially 0.024 inches.

9. A computerized tomographic scanner comprising:
   a generally circular detector arc along which a plurality of radiation detectors are able to be disposed, the radius of the detector arc being the detector radius;
   a radiation source rotatable along a generally circular arc, the radius of the arc being the source radius;
   a collimator comprising an arcuate member interposed between the source and at least some of said detectors, said arcuate member having a plurality of apertures each aperture having a width, the radius of the arcuate member being the collimator radius;
   wherein the improvement comprises the ratio of said source radius to said collimator radius to said collimator aperture width being substantially 24.3:9.4:0.024.

10. The scanner as set forth in claim 9 wherein said radiation detectors are stationarily arranged along the detector arc at 0.5° center-to-center spacings and said collimator apertures are arranged along the arcuate member at 0.3° center-to-center spacings.

11. The scanner as set forth in claim 9 wherein the ratio of said detector radius to said collimator aperature width is generally 36:0.024.

12. The scanner as set forth in claim 11 wherein said collimator aperture width is generally 0.024 inches.

13. In a computerized tomographic scanner having a plurality of radiation detectors positioned along a detector arc, a source of radiation having a focal spot which has a radiation flux distribution, said source being positioned across a scan circle from at least part of the detector arc, and a collimator defining a plurality of apertures arranged in a collimator arc around said source, each aperture having a width in its dimension along the collimator arc, a method of fashioning an efficient collimator aperture width comprising:

(a) determining a first intercept of a first cutting line through the focal spot and a line projected from a point on the detector arc tangent to a first corner of a first aperture of said collimator;

(b) determining a second intercept of said first cutting line and a line projected from said point on the detector arc tangent to a second corner of said first aperture;

(c) summing the radiation flux of the flux distribution along at least that part of the first cutting line within the boundary of the focal spot and between said first and second intercepts to determine an amount of flux impinging on said point;

(d) repeating steps (a), (b), and (c) for another point on the detector arc;

(e) repeating step (d) for points along the detector arc for at least half the distance of the center-to-center spacing of a pair of adjacent detectors;

(f) summing the flux impinging on said points along an arc length at least half the length of a detector;

(g) summing the flux impinging on said points on said detector arc and passing through said first aperture;

(h) finding the ratio of the sum of step (f) to the sum of step (g) to obtain the collimator aperture efficiency;

(i) repeating steps (a) through (h) for each of a plurality of collimator aperture widths; and (j) fashioning the collimator aperture in conformity with the width of the plurality of collimator widths which has the highest collimator aperture efficiency as obtained in steps (a) through (i).

14. The method as set forth in claim 13 further including repeating steps (a), (b) and (c) for at least a second cutting line through the focal spot and summing the flux from the flux distribution of the first and at least the second lines.

15. The method as set forth in claim 13 further including between steps (b) and (c);

determining a third intercept representing the intersection of said first cutting line and a line projected from said point on the detector arc through a third corner of said first aperture;

determining a fourth intercept representing the intersection of said first cutting line and a line projected from said point on the detector arc through a fourth corner of said first aperture;

discarding two of said first, second, third and fourth intercepts whereby step (c) becomes summing the flux along the flux distribution of the first cutting line between the two remaining intercepts.

16. The method as set forth in claim 15 wherein the lines corresponding to the two discarded intercepts intersect said collimator and said two remaining lines traverse said aperture.

17. The method as set forth in claim 13 wherein said tomographic scanner includes a patient scan circle and said source of radiation is a fan of radiation sufficient to span said patent scan circle, said method further including repeating steps (a) through (h) for an aperture positioned in a plurality of positions around the focal spot between the center of said fan and at least one edge of said fan.

18. The method as set forth in claim 13 wherein said flux distribution is $$n_{odd} \Sigma\, a_n \cos \frac{\pi x}{w}$$

wherein $$a_n = \frac{2}{w} \int_o^w g(x) \cos \frac{n\pi x}{w} dx$$

wherein

| $g(x) =$ | $.645/w$ | $0 \leq x \leq .3w$ |
|---|---|---|
| | $1.5625/w$ | $.3w \leq x \leq .5w$ |
| | $-1.5625/w$ | $.5w \leq x \leq .7w$ |
| | $-.625/w$ | $.7w \leq x \leq w$ | and w is the width of said focal spot.

19. The method as set forth in claim 13 wherein said flux distribution is generally $$\frac{1}{w} \cos \frac{\pi x}{w} - \frac{0.8}{w} \cos \frac{3\pi x}{w} + K$$

where K is a constant and where w is the width of the focal spot.

20. A radiographic scanner comprising:

a plurality of radiation detectors disposed in a spaced relationship along a detector arc at center to center intervals of less than 1 degree;

a source of radiation which has a focal spot and a radiation flux distribution across the focal spot, the source being disposed across a scan circle from at least a part of the detector arc to irradiate at least a part of the detector arc;

an arcuate collimator disposed around the source in a collimator arc, the collimator defining a plurality of generally rectangular collimator apertures at least some of said apertures being disposed substantially in the collimator arc between the focal spot and the detector arc, each aperture having a width which is substantially parallel with the collimator arc, the width of each aperture being selected by determining the efficiency of a plurality of aperture widths and selecting the aperture width which has the highest efficiency of said plurality of aperture widths; and drive means for rotating said collimator around the source such that each collimator aperture remains disposed between the source and a corresponding one of the radiation detectors during rotation of the source and the collimator, whereby the collimator defines a plurality of collimated beams of radiation each of which is trained on a corresponding detector during rotation.

21. The scanner as set forth in claim 20 wherein said efficiency is determined by:

(a) determining the amount of radiation impinging on a segment of the detector arc, which segment has a length which is at least one half the center to center interval of the detectors;

(b) determining the amount of radiation impinging upon a part of said segment which corresponds to at least one half a radiation detector; and (c) determining a ratio of the amount of radiation which impinges on said part of said segment to the amount of radiation which impinges on said segment, said efficiency being proportional to said ratio.

22. The scanner as set forth in claim 20 wherein said efficiency is determined by:

(a) determining a first intercept representing the intersection of a first cutting line through the focal spot and a line projected from a point on the detector arc tangent to a first corner of a first aperture of said collimator;

(b) determining a second intercept representing the intersection of said first cutting line and a line projected from said point on the detector arc tangent to a second corner of said first aperture;

(c) summing the radiation flux of the flux distribution along at least that part of the first cutting line within the boundary of the focal spot and between said first and second intercepts to determine an amount of flux impinging on said point;

(d) repeating steps (a), (b), and (c) for another point on the detector arc;

(e) repeating step (d) for points along the detector arc for at least half the distance of the center-to-center spacing of a pair of adjacent detectors;

(f) summing the flux impinging on said points along an arch length at least half the length of a detector;

(g) summing the flux impinging on said points on said detector arc and passing through said first aperture; and, (h) finding the ratio of the sum of step (f) to the sum of step (g) to obtain the collimator aperture efficiency.

23. The scanner as set forth in claim 22 wherein said efficiency is further determined by between steps (b) and (c);

determining a third intercept representing the intersection of said first cutting line and a line projected from said point on the detector arc through a third corner of said first aperture;

determining a fourth intercept representing the intersection of said first cutting line and a line projected from said point on the detector arc through a fourth corner of said first aperture;

discarding two of said first, second, third and fourth intercepts, whereby step (c) becomes summing the flux along the flux distribution of the first cutting line between the two remaining intercepts.

24. A radiographic scanner comprising:

a plurality of radiation detectors disposed in a spaced relationship along a detector arc at center-to-center intervals of 1 degree or less;

a source of radiation which has a focal spot and a radiation flux distribution across the focal spot, the source being disposed across a scan circle from at least a part of the detector arc to irradiate at least the part of the detector arc; and an arcuate collimator disposed around the source in a collimator arc, the collimator defining a plurality of generally rectangular collimator apertures, at least some of said apertures being disposed substantially in the collimator arc between the focal spot and the detector arc, each aperture having a width which is substantially parallel with the collimator arc, the width of each aperture being dimensioned such that a ratio of (a) the total radiation flux impinging on the part of the detector arc to (b) the total radiation flux which impinges upon the radiation detectors along the part of the detector arc is 1 to at least 0.85.

25. The scanner as set forth in claim 24 wherein said ratio is determined by:

(a) determining a first intercept representing the intersection of a first cutting line through the focal spot and a line projected from a point on the detector arc tangent to a first corner of a first aperture of said collimator;

(b) determining a second intercept representing the intersection of the first cutting line through the focal spot and a line projected from the point on the detector arc tangent to a second corner of the first aperture of said collimator;

(c) summing the radiation flux of the flux distribution along at least that part of the first cutting line within the boundary of the focal spot and between said first and second intercepts to determine an amount of flux impinging on said point;

(d) repeating steps (a), (b), and (c) for another point on the detector arc;

(e) repeating step (d) for points along the detector arc for at least half the distance of the center-to-center spacing of a pair of adjacent detectors;

(f) summing the flux impinging on said points along an arc length at least half the length of a detector;

(g) summing the flux impinging on said points on said detector arc and passing through said first aperture; and (h) determining the ratio of the sum of (f) to the sum of (g).

* * * * *

UNITED STATES PATENT AND TRADEMARK OFFICE
CERTIFICATE OF CORRECTION

PATENT NO. : 4,266,135
DATED : May 5, 1981
INVENTOR(S) : John J. Kuwik, et al.

It is certified that error appears in the above-identified patent and that said Letters Patent are hereby corrected as shown below:

Column 13, Line 4, ".645/w" should be --.625/w--

Column 16, Line 10, ".645/w" should be --.625/w--.

Column 17, Line 22, "arch" should be --arc--.

Signed and Sealed this

Eighteenth Day of May 1982

[SEAL]

Attest:

Attesting Officer

GERALD J. MOSSINGHOFF

Commissioner of Patents and Trademarks